(12) United States Patent
DePalma

(10) Patent No.: US 7,189,255 B2
(45) Date of Patent: Mar. 13, 2007

(54) PROSTHESIS SUPPORT RING ASSEMBLY

(75) Inventor: Donald F. DePalma, Weston, FL (US)

(73) Assignee: Cordis Corporation, Miami Lakes, FL (US)

(*) Notice: Subject to any disclaimer, the term of this patent is extended or adjusted under 35 U.S.C. 154(b) by 185 days.

(21) Appl. No.: 10/695,289

(22) Filed: Oct. 28, 2003

(65) Prior Publication Data
US 2005/0090892 A1 Apr. 28, 2005

(51) Int. Cl.
A61F 2/06 (2006.01)

(52) U.S. Cl. ................ 623/1.13; 623/1.12

(58) Field of Classification Search ........ 623/1.12–1.16
See application file for complete search history.

(56) References Cited

U.S. PATENT DOCUMENTS

| | | | |
|---|---|---|---|
| 4,665,906 A | 5/1987 | Jervis | |
| 4,739,762 A | 4/1988 | Palmaz | |
| 4,776,337 A | 10/1988 | Palmaz | |
| 5,385,580 A | 1/1995 | Schmitt et al. | |
| 5,667,523 A * | 9/1997 | Bynon et al. | 623/1.13 |
| 5,749,880 A * | 5/1998 | Banas et al. | 606/198 |
| 5,902,332 A * | 5/1999 | Schatz | 623/1.16 |
| 5,976,183 A * | 11/1999 | Ritz | 623/2.11 |
| 6,099,559 A * | 8/2000 | Nolting | 623/1.16 |
| 6,143,022 A * | 11/2000 | Shull et al. | 623/1.13 |
| 6,254,628 B1 * | 7/2001 | Wallace et al. | 623/1.12 |
| 6,254,632 B1 | 7/2001 | Wu et al. | |
| 6,383,214 B1 * | 5/2002 | Banas et al. | 623/1.14 |
| 6,575,994 B1 | 6/2003 | Marin et al. | |
| 6,887,249 B1 * | 5/2005 | Houser et al. | 606/108 |
| 2001/0020181 A1 | 9/2001 | Layne | |
| 2001/0021870 A1 | 9/2001 | Edwin et al. | |
| 2002/0062147 A1 | 5/2002 | Yang | |
| 2002/0082674 A1 | 6/2002 | Anson et al. | |
| 2004/0204749 A1 * | 10/2004 | Gunderson | 623/1.12 |

FOREIGN PATENT DOCUMENTS

| | | |
|---|---|---|
| EP | 0928606 A1 | 7/1999 |
| EP | 1330993 A1 | 7/2003 |

OTHER PUBLICATIONS

European Search Report EP 04 25 6582 dated Oct. 19, 2005.

* cited by examiner

Primary Examiner—Suzette Gherbi

(57) ABSTRACT

A prosthesis defining a fluid flow path includes a cover and a support assembly supporting the cover. The support assembly includes one or more support structures and each support structure includes an outer portion matingly connected to an inner portion, such that the cover is sandwiched between the outer and inner portions.

6 Claims, 3 Drawing Sheets

PROSTHESIS SUPPORT RING ASSEMBLY

BACKGROUND OF THE INVENTION

1. Field of the Invention

The present invention relates to percutaneously and/or intraluminally delivered devices and methods that include a supported graft material.

2. Discussion of the Related Art

Over the past five years, there has been a great deal of research directed at developing less invasive, endovascular, i.e. catheter directed, techniques for the treatment of a wide variety of conditions, many of which are well known to those skilled in the art. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

While the percutaneous placement of endografts represents a significant improvement over conventional surgical techniques, there is a need to improve the endoprostheses, their method of use, and their applicability to varied biological conditions. Accordingly, in order to provide a safe and effective alternate means for treating aneurysms, including abdominal aortic and thoracic aortic aneurysms, a number of difficulties associated with currently known endoprostheses and their delivery systems must be overcome.

SUMMARY OF THE INVENTION

The support ring assembly of the present invention overcomes the difficulties described above.

In accordance with an aspect of the present invention, a prosthesis includes a cover and a support assembly supporting the cover. The support assembly includes one or more support structures where each support structure comprises an outer portion matingly connected to an inner portion. The cover is sandwiched between the outer and inner portions to provide to provide a structurally sound fluid flow path.

In accordance with another aspect of the present invention, a prosthesis comprises a cover supported by a support assembly. The support assembly includes a plurality of support structures. The cover is looped around the support structure and closed with a connector.

In accordance with still another aspect of the present invention, a prosthesis comprises a cover and a support assembly supporting the cover. The support assembly includes one or more support structures where each support structure comprises a ring having a plurality of radially extending protrusions disposed about a circumference of the ring. The protrusions engage the cover to anchor the support structures to the cover.

The present invention is directed to a support structure for fabricating prostheses that may be utilized in various conduits of the body. Individual flexible support rings may be used in the fabrication of covered stents, stent-grafts, endologs or other devices that require a means to provide radial support to a covering. The individual flexible support rings would be added in the designated section of the graft material by snap fitting one ring inside the other, thereby sandwiching the graft material therebetween.

The present invention offers a number of advantages over existing prostheses. The individual ring structure of the present invention would allow for increased manufacturing speeds. By sandwiching the graft material between support rings, no breech or puncture of the graft is required for attachment. The individual flexible support rings are isolated from one another so that if they are formed from metallic materials, any potential for corrosion is eliminated. The individual flexible rings would provide radial support while allowing the graft material to flex, thereby increasing the flexibility of the composite structure while reducing the potential for kinking. The individual flexible rings allow for the graft to be easily crimped and placed into a delivery system. In addition, since the individual flexible support rings may be snap fit onto the graft material, the relative motion between the graft and the rings would be minimized, thereby reducing or minimizing potential graft wear.

The accompanying figures show illustrative embodiments of the present invention from which these and other of the objectives, novel features and advantages will be readily apparent.

BRIEF DESCRIPTION OF THE DRAWINGS

The foregoing and other aspects of the present invention will best be appreciated with reference to the detailed description of the invention in conjunction with the accompanying drawings. Throughout the figures and the description below, like numerals indicate the same element.

FIG. 1 is a side perspective view of a support assembly.

DETAILED DESCRIPTION OF THE PREFERRED EMBODIMENTS

Figure 1A:
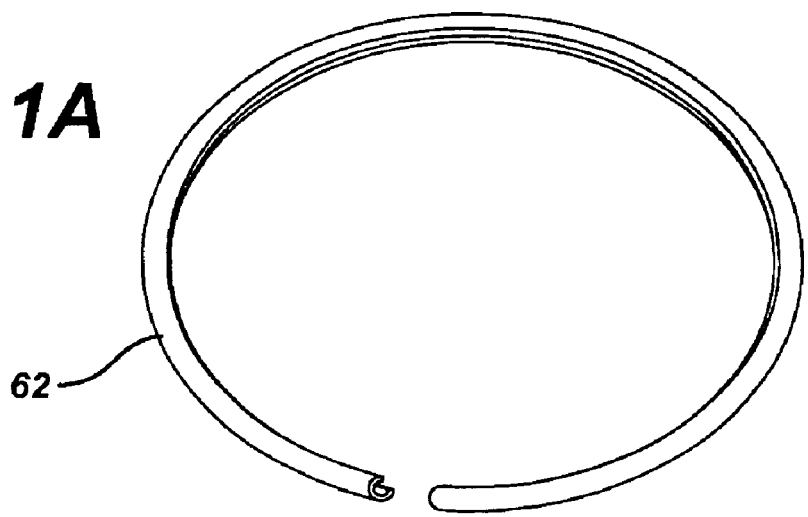
FIG. 1A is the external portion.
Figure 1B:
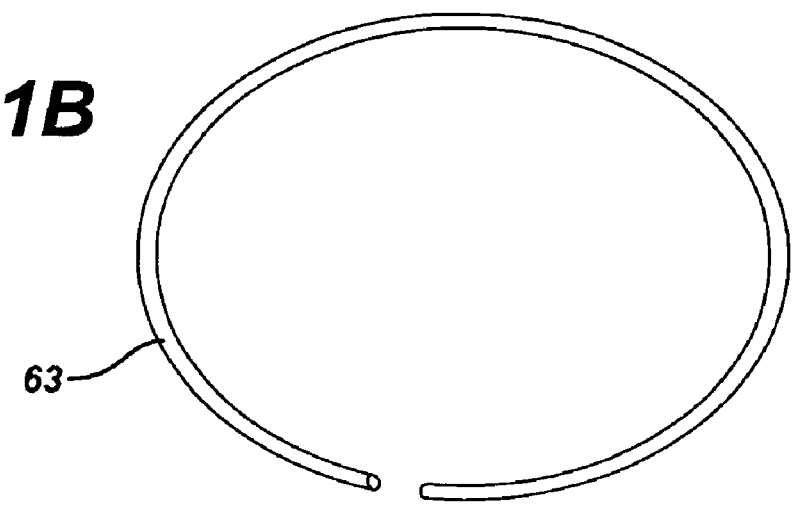
FIG. 1B is the internal portion.
Figure 1C:
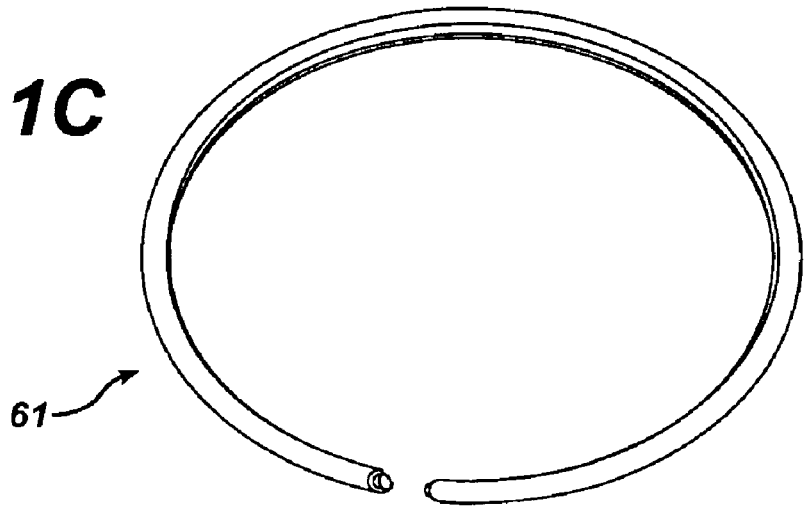
FIG. 1C shows the integrated support assembly.
Figure 2:
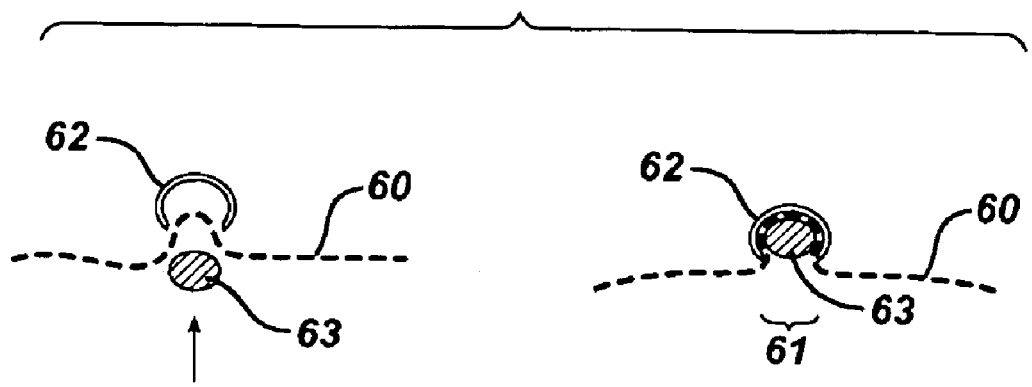
FIG. 2 is a perspective view of a support assembly locking a graft material in place.

The present invention is directed to a method and means for providing support to graft material in order to maintain lumen patency by utilizing individual flexible support rings rather than conventional stents. Because these individual flexible support rings may be snap fit onto the graft material, the relative motion between the graft and supporting rings would be minimized, thereby reducing or substantially eliminating graft wear. These individual flexible support rings may be fabricated or constructed from any number of metals or metal alloys, including those exhibiting shape memory or superelastic qualities or any other suitable biocompatible, flexible materials, including polymers and elastomers.

The individual flexible support rings may be used in the fabrication or construction of covered stents, stent-grafts, endologs or other devices that require a means to provide radial support to a covering. The individual flexible support rings would be added in the designated section of the graft material by snap fitting one ring inside the other, thereby sandwiching the graft material between the two rings as described in detail subsequently.

A better understanding of the present device and its use will be achieved by reading the following description in conjunction with the above-incorporated references.

The present invention is directed to a system, apparatus, method, and respective components for establishing a fluid path from one portion of an artery into another portion of the arterial network. The present invention may also be utilized in other lumens of the body.

A prosthesis in accordance with the present invention comprises a graft material supported by a support assembly of the present invention. Exemplary prostheses include covered stents, stent grafts, endolegs and other devices that require means to provide radial support for a covering.

In one exemplary embodiment of the present invention, a support assembly comprises an outer portion and an inner portion, the inner portion configured to nest or interlock within the internal diameter of the outer portion. The graft material or the gasket material may be positioned or sandwiched between the outer portion and the inner portion of the support assembly. In preferred embodiments of the invention, the graft material or the gasket material does not need to be punctured, e.g., with sutures, to attach the graft material to the support assembly.

An alternate exemplary embodiment of the present invention comprises only the inner portion, as described above. In this exemplary embodiment of the present invention, a loop of the graft material or the gasket material passes over the inner portion, and a connector or the like holds or binds the inner portion in place.

Each of the components of the system will now be described in more detail. Any references to the Figures will be used to illustrate one or more exemplary embodiments of the invention, without intending to limit the invention thereby.

A prosthesis of the present invention includes a support assembly covered by or supporting at least one covering material, such as a graft material. The support assembly and cover material define an interior space having an open proximal end and an open distal end. The graft material may comprise a wide variety of materials, may be configured in a wide variety of shapes, and their shapes and uses are well known in the art. Exemplary materials for use with this aspect of the invention are disclosed in U.S. Pat. No. 4,739,762 (Palmaz) and U.S. Pat. No. 4,776,337 (Palmaz).

In accordance with the present invention, the support assembly may be variously configured. In preferred embodiments of the invention, the support assembly comprises a plurality of support structures each having an outer portion and an inner portion, both of which are complementary structures between which a graft material or gasket material may be sandwiched. In the exemplary embodiments shown in FIGS. 1–4, support structure 61 comprises an outer portion in the form of an outer ring 62 and an inner portion in the form of an inner ring 63.

In accordance with the present invention, the outer portion may be variously configured. Any structure or shape having a void is suitable. In preferred embodiments of the invention, the outer portion is a ring 62, preferably an openable resilient, flexible ring.

In accordance with the present invention, the inner portion may be variously configured. Any structure or shape configured to complement the void in the outer portion is suitable. In preferred embodiments of the invention, the inner portion is a ring 63, preferably an openable resilient, flexible ring.

In keeping with the invention, outer ring 62 and inner ring 63 are preferably matingly connected to each other. More preferably, outer ring 62 and inner ring 63 are snap-fit to each other. The graft material is preferably sandwiched and anchored between the inner and outer portions. Advantageously, in this embodiment, the graft material is anchored to the support assembly without puncturing the graft material. The flexibility of the inner and outer portions allows the graft material to flex which increases the flexibility of the prosthesis while reducing the potential for kinking. In addition, the flexibility of the inner and outer portions allows the prosthesis to be readily crimped and placed into a delivery system.

Figure 6:
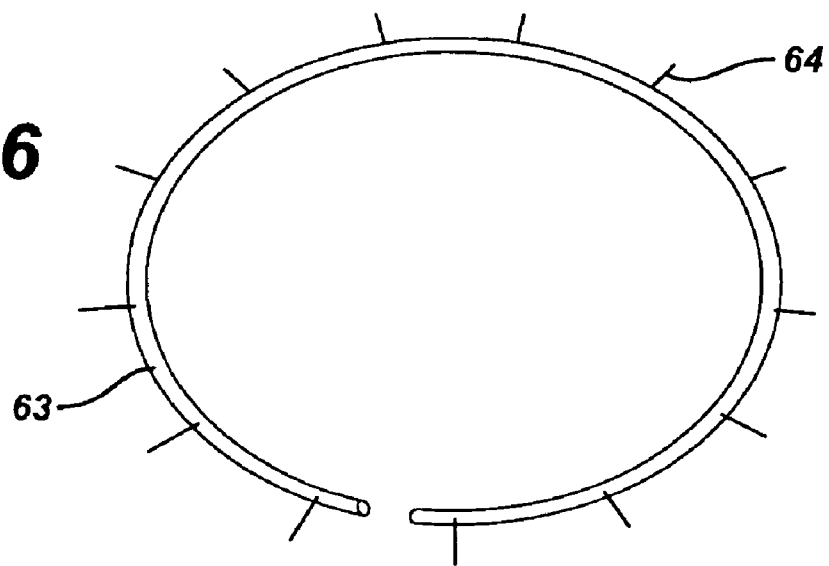
FIG. 6 is an alternative embodiment of an inner ring of the invention.

One skilled in the art will readily recognize that an inner or outer portion of the support assembly may be configured or adapted to include certain features and/or to perform a certain function(s), and that alternate designs may be used to promote those features or functions. For example, the interior surface of the outer portion and/or the outer surface of the inner portion may include one or more protrusions, e.g., ribs, spikes, nubs, or the like. The preferred alternative structure is shown in FIG. 6, in which the inner ring 63 includes one or more spikes 64. These protrusions are intended to engage the graft or gasket material so as to anchor the graft material to the ring, either by abutting the graft material, or by passing through the graft material.

Figure 5:
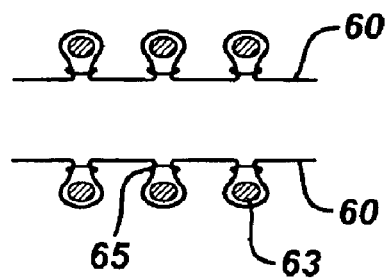
FIG. 5 is an alternative embodiment of the invention.

Alternatively, a graft or gasket material may be supported using only a structure as defined above for the inner portion. In these exemplary embodiments of the present invention, the graft material may be looped around the inner portion, and a clamp or suture or the like may be used to capture the inner portion in place. The exemplary structure shown in FIG. 5 shows graft material 60 looped around inner portion 63, which is held in place using sutures. A graft material may be attached to a support structure by any number of structures or methods known to those skilled in the art, including adhesives, such as polyurethane glue; a plurality of conventional sutures of polyvinylidene fluoride, polypropylene, Dacron®, or any other suitable material; ultrasonic welding; mechanical interference fit; and staples.

In one exemplary embodiment, one or more rings may be radiopaque for increased visibility through the vasculature. In another exemplary embodiment, the proximal and distal rings have greater radial and longitudinal strength than the rings therebetween. This creates a porsthesis having stiff ends for anchoring, but a more flexible body for navigation through the vasculature. The stiffer ends may be accomplished by changing the stiffness of the ring or clip, or by varying the heat treatment of the end rings during manufacture. The rings allow the prosthesis to bend more easily, and generally provide for more flexibility when the prosthesis is being delivered through a tortuous vessel. When a non-compliant graft is attached to a support, the strength of the support assembly scaffolds any graft from folding into the blood flow lumen, while maintaining a tight kink radius.

Any of the support assembly structures of the present invention may be formed of any material suitable for functioning in vivo as a support for graft material. A support structure of the present invention may be formed of a wide variety of materials, all of which are well known to those skilled in the art. In some exemplary embodiments of the invention, the inner and outer ring may be formed from a metal or metal alloy. In preferred embodiments of the invention, the support structure's may be formed from superelastic Nickel Titanium alloys (Nitinol). Descriptions of medical devices which use such alloys can be found in U.S. Pat. No. 4,665,906 and European Patent Application EP 0928606, both of which are hereby incorporated herein by reference. A support structure according to the present invention is preferably laser cut from a piece of nitinol and thereafter treated so as to exhibit shaped memory properties at body temperature.

The graft material may be variously configured, preferably to achieve predetermined mechanical properties. For example, the graft material may incorporate a single or multiple weaving and/or pleating patterns, or may be pleated or unpleated. For example, the graft may be configured into a plain weave, a satin weave, include continuous longitudinal pleats, interrupted pleats, annular or helical pleats, radially oriented pleats, or combinations thereof. Alternately, the graft material may be knitted or braided. In the exemplary embodiments of the invention in which the graft material is pleated, the pleats may be continuous or discontinuous. Also, the pleats may be oriented longitudinally, circumferentially, or combinations thereof.

Placing one portion of the support assembly closer together on the graft material forms a curve in the prosthesis. Compare FIGS. 3 and 4. As shown, maintaining an equal length of graft material between successive support assemblies forms a straight segment (see FIG. 3). Providing a shorter length of graft material in one area of the support assembly as compared to another area allows the prosthesis to bend (see FIG. 4).

Figure 3:
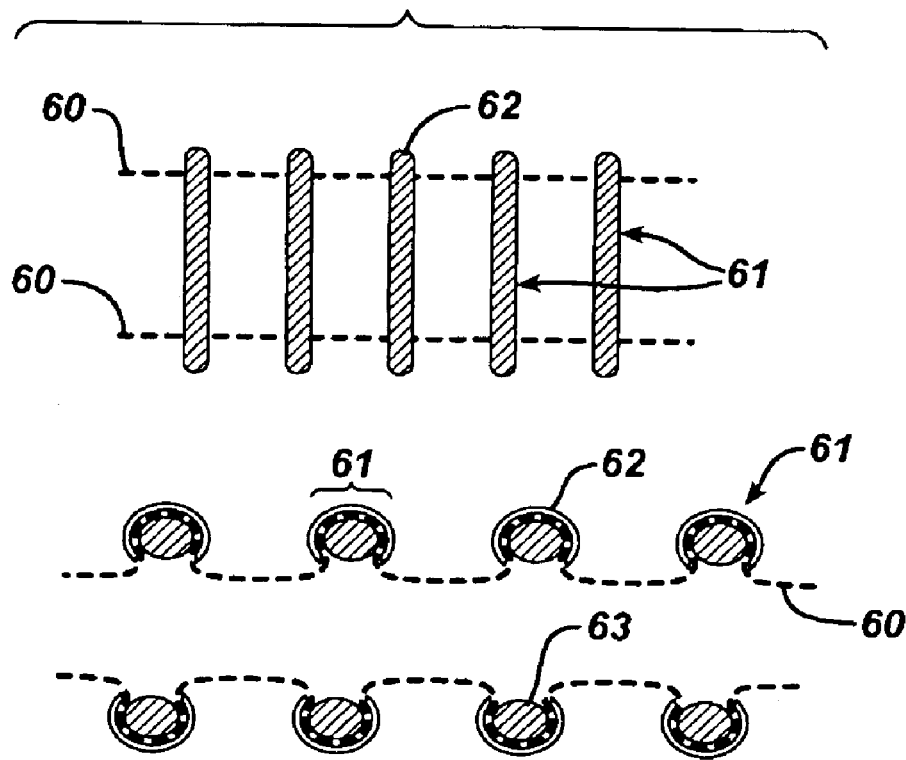
FIG. 3 is a perspective view of a straight portion of a prosthesis.
Figure 4:
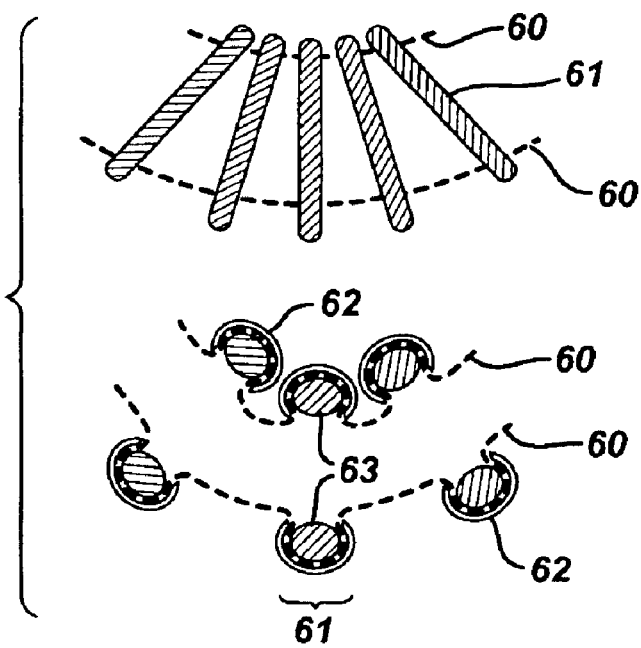
FIG. 4 is a perspective view of a curved or angular portion of a prosthesis.

In order to reduce or eliminate corrosion problems, it is desirable to metallically isolate support assemblies 61 from other metallic components. Accordingly, as illustrated in FIG. 3, support structures 61 are spaced from each other.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A prosthesis defining a fluid flow path comprising: a cover and a support assembly supporting the cover, the support assembly including one or more support structures, each support structure including an outer portion and an inner portion, the inner portion of the support structure being configured to interlock with the outer portion of the support structure through a snap fit, said cover being sandwiched between the outer and inner portions of said support structure;

wherein the assembly is configured with a luminal fluid flow pathway.

2. The prosthesis of claim 1 wherein said support assembly and cover define a fluid flow path though the prosthesis.

3. The prosthesis of claim 1 wherein the support assembly is formed from at least one metal.

4. The prosthesis of claim 3 wherein the support assembly is formed from a nickel titanium alloy.

5. The prosthesis of claim 4 wherein the support assembly is formed from nitinol.

6. The prosthesis of claim 1 wherein the outer portion of the support structure comprises a metal ring and the inner portion of the support structure comprises a metal ring.

* * * * *